US009186075B2

(12) United States Patent
Baker, Jr. et al.

(10) Patent No.: US 9,186,075 B2
(45) Date of Patent: Nov. 17, 2015

(54) INDICATING THE ACCURACY OF A PHYSIOLOGICAL PARAMETER

(75) Inventors: Clark R. Baker, Jr., Newman, CA (US);
Lutz Andersohn, Glencoe, MO (US);
Paul Mannheimer, Danville, CA (US)

(73) Assignee: Covidien LP, Mansfield, MA (US)

(*) Notice: Subject to any disclaimer, the term of this patent is extended or adjusted under 35 U.S.C. 154(b) by 1973 days.

(21) Appl. No.: 12/409,704

(22) Filed: Mar. 24, 2009

(65) Prior Publication Data

US 2010/0249549 A1  Sep. 30, 2010

(51) Int. Cl.
*A61B 5/00* (2006.01)
*A61B 5/024* (2006.01)
*A61B 5/1455* (2006.01)

(52) U.S. Cl.
CPC ........... *A61B 5/02416* (2013.01); *A61B 5/7221* (2013.01); *A61B 5/7415* (2013.01); *A61B 5/1455* (2013.01); *A61B 5/742* (2013.01)

(58) Field of Classification Search
CPC ............. A61B 5/02416; A61B 5/7415; A61B 5/7221; A61B 5/1455; A61B 5/742
USPC ............... 600/483, 300, 301, 309–344; 7/300
See application file for complete search history.

(56) References Cited

U.S. PATENT DOCUMENTS

| | | | |
|---|---|---|---|
| 4,752,089 A * | 6/1988 | Carter | 285/276 |
| 4,863,265 A * | 9/1989 | Flower et al. | 356/41 |
| 4,921,642 A * | 5/1990 | LaTorraca | 261/142 |
| 4,954,799 A * | 9/1990 | Kumar | 335/236 |
| 5,057,822 A * | 10/1991 | Hoffman | 340/611 |
| 5,072,737 A * | 12/1991 | Goulding | 600/531 |
| 5,107,831 A | 4/1992 | Halpern et al. | |
| 5,150,291 A * | 9/1992 | Cummings et al. | 128/204.23 |
| 5,158,534 A | 10/1992 | Berry et al. | |
| 5,161,525 A * | 11/1992 | Kimm et al. | 128/204.26 |
| 5,199,439 A * | 4/1993 | Zimmerman et al. | 600/483 |
| 5,237,987 A * | 8/1993 | Anderson et al. | 128/204.18 |
| 5,271,389 A * | 12/1993 | Isaza et al. | 128/204.21 |
| 5,279,549 A * | 1/1994 | Ranford | 604/34 |
| 5,299,568 A * | 4/1994 | Forare et al. | 128/205.11 |
| 5,325,861 A * | 7/1994 | Goulding | 600/532 |
| 5,333,606 A * | 8/1994 | Schneider et al. | 128/200.24 |
| 5,339,807 A * | 8/1994 | Carter | 128/205.24 |
| 5,351,522 A * | 10/1994 | Lura | 73/24.01 |
| 5,355,893 A | 10/1994 | Mick et al. | |
| 5,357,946 A * | 10/1994 | Kee et al. | 128/200.24 |
| 5,368,019 A * | 11/1994 | Latorraca | 128/204.18 |

(Continued)

*Primary Examiner* — Sean Dougherty
(74) *Attorney, Agent, or Firm* — Fletcher Yoder PC (57) ABSTRACT

This disclosure describes systems and methods for displaying information that describes the accuracy of estimated values of physiological parameters. As part of the process of estimating a physiological parameter, the data used for the estimation are further analyzed to determine one or more statistical parameters indicative of the accuracy of the estimate. These statistical parameters are then displayed to the caregiver in order to provide the caregiver additional information concerning the estimated value. In the systems and methods described herein, one or more probability analyses are performed on the data used to generate the estimate of the physiological parameter. The analyses may include calculating the accuracy, confidence interval or some other statistical parameter representative of the accuracy of the estimate of the physiological parameter from the variations in the data An indication of the accuracy and/or an indication of the calculated probability may then be displayed to a caregiver or user.

20 Claims, 9 Drawing Sheets

(56) References Cited

U.S. PATENT DOCUMENTS

| | | | |
|---|---|---|---|
| 5,385,142 A * | 1/1995 | Brady et al. ............. 128/204.23 |
| 5,390,666 A * | 2/1995 | Kimm et al. ............. 128/204.26 |
| 5,401,135 A * | 3/1995 | Stoen et al. .................. 414/546 |
| 5,402,796 A * | 4/1995 | Packer et al. ................ 600/532 |
| 5,407,174 A * | 4/1995 | Kumar .................... 251/129.08 |
| 5,438,980 A * | 8/1995 | Phillips ..................... 128/204.23 |
| 5,443,075 A * | 8/1995 | Holscher ...................... 600/538 |
| 5,513,631 A * | 5/1996 | McWilliams ............ 128/204.23 |
| 5,517,983 A * | 5/1996 | Deighan et al. .......... 128/204.23 |
| 5,520,071 A * | 5/1996 | Jones ............................. 74/557 |
| 5,520,192 A | 5/1996 | Kitney et al. |
| 5,524,615 A * | 6/1996 | Power ....................... 128/205.12 |
| 5,531,221 A * | 7/1996 | Power et al. ............. 128/205.18 |
| 5,534,851 A | 7/1996 | Russek |
| 5,542,415 A * | 8/1996 | Brody ....................... 128/204.23 |
| 5,544,674 A * | 8/1996 | Kelly ............................... 137/98 |
| 5,549,106 A * | 8/1996 | Gruenke et al. .......... 128/204.23 |
| 5,590,648 A | 1/1997 | Mitchell et al. |
| 5,596,984 A * | 1/1997 | O'Mahony et al. ...... 128/205.24 |
| 5,598,838 A | 2/1997 | Servidio et al. |
| 5,611,335 A | 3/1997 | Makhoul et al. |
| 5,632,270 A * | 5/1997 | O'Mahony et al. ...... 128/204.24 |
| 5,645,048 A * | 7/1997 | Brodsky et al. .......... 128/202.27 |
| 5,664,560 A * | 9/1997 | Merrick et al. ........... 128/203.25 |
| 5,664,562 A * | 9/1997 | Bourdon .................. 128/204.23 |
| 5,672,041 A * | 9/1997 | Ringdahl et al. .............. 414/545 |
| 5,673,689 A * | 10/1997 | Power ....................... 128/205.18 |
| 5,678,539 A | 10/1997 | Schubert et al. |
| 5,752,506 A | 5/1998 | Richardson |
| 5,762,480 A * | 6/1998 | Adahan ........................ 417/415 |
| 5,771,884 A * | 6/1998 | Yarnall et al. ............ 128/205.24 |
| 5,791,339 A * | 8/1998 | Winter ..................... 128/202.22 |
| 5,794,986 A * | 8/1998 | Gansel et al. .............. 285/148.16 |
| 5,813,399 A * | 9/1998 | Isaza et al. ............... 128/204.21 |
| 5,819,723 A | 10/1998 | Joseph |
| 5,826,575 A * | 10/1998 | Lall .......................... 128/205.12 |
| 5,829,441 A * | 11/1998 | Kidd et al. ...................... 128/848 |
| 5,865,168 A * | 2/1999 | Isaza ......................... 128/200.24 |
| 5,881,717 A * | 3/1999 | Isaza ........................ 128/202.22 |
| 5,881,723 A * | 3/1999 | Wallace et al. ........... 128/204.21 |
| 5,915,379 A | 6/1999 | Wallace et al. |
| 5,918,597 A * | 7/1999 | Jones et al. ............... 128/205.18 |
| 5,921,238 A * | 7/1999 | Bourdon .................. 128/204.23 |
| 5,931,160 A | 8/1999 | Gilmore et al. |
| 5,956,023 A | 9/1999 | Lyle et al. |
| 5,966,760 A | 10/1999 | Gallant et al. |
| 6,024,089 A | 2/2000 | Wallace et al. |
| 6,041,780 A * | 3/2000 | Richard et al. ........... 128/204.18 |
| 6,047,860 A * | 4/2000 | Sanders ............................ 222/3 |
| 6,076,523 A * | 6/2000 | Jones et al. ................ 128/205.11 |
| 6,123,073 A * | 9/2000 | Schlawin et al. ......... 128/204.21 |
| 6,133,994 A * | 10/2000 | Mathews et al. ................. 356/41 |
| 6,135,106 A * | 10/2000 | Dirks et al. ............... 128/204.23 |
| 6,142,150 A * | 11/2000 | O'Mahoney ............. 128/205.18 |
| 6,203,502 B1 | 3/2001 | Hilgendorf et al. |
| 6,220,245 B1 * | 4/2001 | Takabayashi et al. ... 128/205.12 |
| 6,269,812 B1 | 8/2001 | Wallace et al. |
| 6,273,444 B1 * | 8/2001 | Power ......................... 280/304.1 |
| 6,283,119 B1 * | 9/2001 | Bourdon .................. 128/204.23 |
| 6,305,373 B1 | 10/2001 | Wallace et al. |
| 6,321,748 B1 * | 11/2001 | O'Mahoney ............. 128/204.21 |
| 6,325,785 B1 * | 12/2001 | Babkes et al. ................. 604/319 |
| 6,357,438 B1 * | 3/2002 | Hansen .................... 128/204.18 |
| 6,369,838 B1 | 4/2002 | Wallace et al. |
| 6,390,091 B1 | 5/2002 | Banner et al. |
| 6,406,426 B1 | 6/2002 | Reuss et al. |
| 6,439,229 B1 * | 8/2002 | Du et al. ................... 128/204.23 |
| 6,546,930 B1 * | 4/2003 | Emerson et al. .......... 128/204.21 |
| 6,557,553 B1 * | 5/2003 | Borrello ................... 128/204.18 |
| 6,575,902 B1 | 6/2003 | Burton |
| 6,579,232 B2 | 6/2003 | Sakamaki et al. |
| 6,622,726 B1 * | 9/2003 | Du ........................... 128/204.26 |
| 6,644,310 B1 * | 11/2003 | Delache et al. ........... 128/204.21 |
| 6,675,031 B1 * | 1/2004 | Porges et al. ................. 600/322 |
| 6,718,974 B1 * | 4/2004 | Moberg .................... 128/204.14 |
| 6,725,447 B1 * | 4/2004 | Gilman et al. ................. 717/105 |
| 6,761,167 B1 * | 7/2004 | Nadjafizadeh et al. .. 128/204.23 |
| 6,761,168 B1 * | 7/2004 | Nadjafizadeh et al. .. 128/204.23 |
| 6,796,305 B1 | 9/2004 | Banner et al. |
| 6,814,074 B1 * | 11/2004 | Nadjafizadeh et al. .. 128/204.23 |
| 6,836,679 B2 * | 12/2004 | Baker et al. .................... 600/323 |
| 6,866,040 B1 * | 3/2005 | Bourdon .................. 128/204.18 |
| 6,876,303 B2 | 4/2005 | Reeder et al. |
| 6,956,572 B2 | 10/2005 | Zaleski |
| 6,960,854 B2 * | 11/2005 | Nadjafizadeh et al. ......... 310/89 |
| 7,036,504 B2 | 5/2006 | Wallace et al. |
| 7,044,930 B2 | 5/2006 | Strömberg |
| 7,077,131 B2 * | 7/2006 | Hansen .................... 128/204.18 |
| RE39,225 E * | 8/2006 | Isaza et al. ............... 128/202.22 |
| 7,117,438 B2 | 10/2006 | Wallace et al. |
| 7,162,296 B2 | 1/2007 | Leonhardt et al. |
| 7,210,478 B2 | 5/2007 | Banner et |
| 7,237,205 B2 | 6/2007 | Sarel |
| 7,263,995 B2 | 9/2007 | Gurneé et al. |
| 7,270,126 B2 | 9/2007 | Wallace et al. |
| 7,290,544 B1 | 11/2007 | Särelä et al. |
| 7,320,321 B2 | 1/2008 | Pranger et al. |
| 7,327,219 B2 | 2/2008 | Lederer, IV |
| 7,343,917 B2 | 3/2008 | Jones |
| 7,369,757 B2 * | 5/2008 | Farbarik ........................ 388/806 |
| 7,428,902 B2 * | 9/2008 | Du et al. ................... 128/204.17 |
| 7,460,959 B2 * | 12/2008 | Jafari ............................ 702/24 |
| 7,487,773 B2 * | 2/2009 | Li ............................. 128/204.18 |
| 7,654,802 B2 * | 2/2010 | Crawford et al. ............. 417/415 |
| 7,694,677 B2 * | 4/2010 | Tang ........................ 128/204.18 |
| 7,721,736 B2 | 5/2010 | Urias et al. |
| 7,784,461 B2 * | 8/2010 | Figueiredo et al. ...... 128/204.23 |
| 7,855,716 B2 * | 12/2010 | McCreary et al. ............. 345/173 |
| D632,796 S * | 2/2011 | Ross et al. .................... D24/185 |
| D632,797 S * | 2/2011 | Ross et al. .................... D24/185 |
| 7,891,354 B2 * | 2/2011 | Farbarik .................. 128/204.21 |
| 7,893,560 B2 * | 2/2011 | Carter ............................. 307/64 |
| 7,984,714 B2 * | 7/2011 | Hausmann et al. ........... 128/848 |
| 8,021,310 B2 * | 9/2011 | Sanborn et al. ................ 600/538 |
| 8,181,648 B2 * | 5/2012 | Perine et al. ............. 128/204.18 |
| 8,210,173 B2 * | 7/2012 | Vandine .................. 128/204.21 |
| 8,210,174 B2 * | 7/2012 | Farbarik .................. 128/204.21 |
| 8,272,380 B2 * | 9/2012 | Jafari et al. .............. 128/204.21 |
| 8,302,600 B2 * | 11/2012 | Andrieux et al. ........ 128/202.22 |
| 8,302,602 B2 * | 11/2012 | Andrieux et al. ........ 128/204.22 |
| 2002/0026941 A1 | 3/2002 | Biondi et al. |
| 2004/0133123 A1 | 7/2004 | Leonhardt et al. |
| 2004/0221845 A1 | 11/2004 | Pranger et al. |
| 2005/0033124 A1 | 2/2005 | Kelly et al. |
| 2005/0039748 A1 * | 2/2005 | Andrieux .................. 128/204.22 |
| 2005/0061321 A1 | 3/2005 | Jones |
| 2005/0098178 A1 | 5/2005 | Banner et al. |
| 2005/0172966 A1 | 8/2005 | Blaise et al. |
| 2006/0258929 A1 * | 11/2006 | Goode et al. .................. 600/345 |
| 2007/0000494 A1 | 1/2007 | Banner et al. |
| 2007/0017515 A1 | 1/2007 | Wallace et al. |
| 2007/0077200 A1 * | 4/2007 | Baker ............................ 424/9.1 |
| 2007/0227537 A1 * | 10/2007 | Bemister et al. ......... 128/200.24 |
| 2007/0284361 A1 * | 12/2007 | Nadjafizadeh et al. ....... 219/442 |
| 2008/0033254 A1 * | 2/2008 | Kamath et al. ............... 600/300 |
| 2008/0053441 A1 * | 3/2008 | Gottlib et al. ............ 128/204.23 |
| 2008/0072896 A1 * | 3/2008 | Setzer et al. .............. 128/200.24 |
| 2008/0072902 A1 * | 3/2008 | Setzer et al. .............. 128/204.21 |
| 2008/0078390 A1 * | 4/2008 | Milne et al. .............. 128/204.23 |
| 2008/0083644 A1 * | 4/2008 | Janbakhsh et al. ............. 206/703 |
| 2008/0092894 A1 * | 4/2008 | Nicolazzi et al. ........ 128/204.23 |
| 2008/0097143 A1 | 4/2008 | Califorrniaa |
| 2008/0097234 A1 * | 4/2008 | Nicolazzi et al. ............. 600/538 |
| 2009/0165795 A1 * | 7/2009 | Nadjafizadeh et al. .. 128/204.18 |
| 2009/0171176 A1 * | 7/2009 | Andersohn .................. 600/324 |
| 2009/0205661 A1 * | 8/2009 | Stephenson et al. ..... 128/204.21 |
| 2009/0205663 A1 * | 8/2009 | Vandine et al. .......... 128/204.23 |
| 2009/0247848 A1 * | 10/2009 | Baker, Jr. ...................... 600/323 |
| 2010/0011307 A1 * | 1/2010 | Desfossez et al. ............. 715/764 |
| 2010/0071689 A1 * | 3/2010 | Thiessen .................. 128/202.22 |
| 2010/0071695 A1 * | 3/2010 | Thiessen .................. 128/204.18 |
| 2010/0071696 A1 * | 3/2010 | Jafari ....................... 128/204.23 |
| 2010/0078017 A1 * | 4/2010 | Andrieux et al. ........ 128/202.22 |
| 2010/0078026 A1 * | 4/2010 | Andrieux et al. ........ 128/204.21 |

(56) References Cited

U.S. PATENT DOCUMENTS

| | | | |
|---|---|---|---|
| 2010/0081119 A1* | 4/2010 | Jafari et al. | 434/272 |
| 2010/0081955 A1* | 4/2010 | Wood et al. | 600/532 |
| 2010/0139660 A1* | 6/2010 | Adahan | 128/205.24 |
| 2010/0147303 A1* | 6/2010 | Jafari et al. | 128/204.23 |
| 2010/0218765 A1* | 9/2010 | Jafari et al. | 128/204.21 |
| 2010/0218766 A1* | 9/2010 | Milne | 128/204.23 |
| 2010/0218767 A1* | 9/2010 | Jafari et al. | 128/204.23 |

* cited by examiner

INDICATING THE ACCURACY OF A PHYSIOLOGICAL PARAMETER

BACKGROUND

In medicine, a plethysinograph is an instrument that measures physiological parameters, such as variations in the size of an organ or body part, through an analysis of the blood passing through or present in the targeted body part, or a depiction of these variations. An oximeter is an instrument that determines the oxygen saturation of the blood. One common type of oximeter is a pulse oximeter, which determines oxygen saturation by analysis of an optically sensed plethysmograph.

A pulse oximeter is a medical device that indirectly measures the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient.

A pulse oximeter may include a light sensor that is placed at a site on a patient, usually a fingertip, toe, forehead or earlobe, or in the case of a neonate, across a foot. Light, which may be produced by a light source integrated into the pulse oximeter, containing both red and infrared wavelengths is directed onto the skin of the patient and the light that passes through the skin is detected by the sensor. The intensity of light in each wavelength is measured by the sensor over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths at different points in the pulse cycle, it is possible to estimate the blood oxygen saturation of hemoglobin in arterial blood. This relies on the observation that highly oxygenated blood will absorb relatively less red light and more infrared light than blood with lower oxygen saturation.

SUMMARY

This disclosure describes systems and methods for indicating the accuracy of a measured physiological parameter, such as the pulsatile oxygen saturation ($SpO_2$) measurement generated by a pulse oximeter, to a user. As discussed in greater detail below, the disclosure describes methods for displaying the measured oxygen saturation of a patient's blood in way that quantitatively depicts the likelihood that the measurement is above or below values. The likelihood is determined based at least in part upon the quality of the data from which the oxygen saturation is determined. In an embodiment, the disclosure describes a method for the real-time display of a physiological parameter. The method may include displaying a first indicator identifying an estimated value of the physiological parameter and simultaneously displaying a second indicator describing a probability distribution of the physiological parameter. The indicators may be graphical or numerical or audible or a combination thereof and presented on an interface in a manner that makes the information easily understandable by the user. The method may further include identifying a predetermined confidence level, displaying at least one of an upper limit or a lower limit of a confidence interval calculated based on the predetermined confidence level and the physiological data used to generate the estimated value.

The disclosure further describes an embodiment of a method for displaying oxygen saturation of a patient's blood that includes calculating an estimated value of the oxygen saturation of the patient's blood based on information received from a sensor and displaying the estimated value on a user interface. In addition, the method further includes calculating at least one statistical parameter based on information received from the sensor and displaying the at least one statistical parameter with the estimated value simultaneously on the user interface. The method may further include displaying at least one of an upper limit of a confidence interval and a lower limit of the confidence level, in which the displayed confidence interval limit(s) are calculated based on a predetermined confidence level and information received from the sensor.

The disclosure further describes an embodiment of a pulse oximeter that includes a microprocessor capable of calculating an estimated value of oxygen saturation of a patient's blood from information received from a sensor and further capable of calculating at least one statistical parameter based on information received from the sensor. The plethysmograph further includes a display capable of displaying the estimated value of the oxygen saturation of the patient's blood and the at least one statistical parameter. The statistical parameters displayed may be selected from an upper limit of a confidence interval, a lower limit of the confidence interval, and an accuracy of the estimated value. The display may also be capable simultaneously displaying the upper limit of the confidence interval, the lower limit of the confidence interval, and the accuracy of the estimated value. In addition, the plethysmograph may include a user interface capable of receiving a user selection of a confidence level for use in calculating the upper limit of the confidence interval and the lower limit of the confidence interval and memory capable of storing the user selection. The plethysmograph may also include an accuracy module capable of calculating the accuracy of the estimated value and a statistical analysis module capable of calculating at least one of the upper limit or lower limit of the confidence interval based on information received from the sensor and a stored confidence level.

These and various other features as well as advantages which characterize the disclosed systems and methods will be apparent from a reading of the following detailed description and a review of the associated drawings. Additional features of the systems and methods described herein are set forth in the description which follows, and in part will be apparent from the description, or may be learned by practice of the technology. The benefits and features will be realized and attained by the structure particularly pointed out in the written description and claims as well as the appended drawings.

It is to be understood that both the foregoing general description and the following detailed description are exemplary and explanatory and are intended to provide further explanation of the disclosed technology as claimed.

BRIEF DESCRIPTION OF THE DRAWINGS

The following drawing figures, which form a part of this application, are illustrative of disclosed technology and are not meant to limit the scope of the description in any manner, which scope shall be based on the claims appended hereto.

DETAILED DESCRIPTION

This disclosure describes systems and methods for displaying information that describes the accuracy of estimated values of physiological parameters. In an embodiment, as part of the process of estimating the value of a physiological parameter, the data from which the value is derived are further analyzed to determine one or more statistical parameters indicative of the accuracy of the estimate. These statistical parameters may then be displayed to the caregiver in order to provide the caregiver additional information concerning the estimated value.

In the systems and methods described herein, one or more probability analyses may be performed on the data used to generate the estimate of the physiological parameter. The analyses may include calculating the accuracy, confidence interval or some other statistical parameter representative of the accuracy of the estimate of the physiological parameter from the variations in the data. An indication of the accuracy and/or an indication of the calculated probability may then be displayed to a caregiver or user.

Although the techniques for calculating, using and displaying statistical parameters associated with an estimated physiological parameter introduced above and discussed in detail below may be implemented for a variety of medical devices and physiological parameters, the present disclosure will discuss the implementation of these techniques in a pulse oximeter. Although described in detail in this context of a pulse oximeter displaying oxygen saturation measurements, the reader will understand that the systems and methods described herein may be equally adapted to the estimation and display of any physiological parameter of any patient (human or non-human) generated by any monitoring device, including but not limited to blood pressure, temperature, cardiac output, respiration parameters, and measures of blood constituents other than oxygenation.

Figure 1:
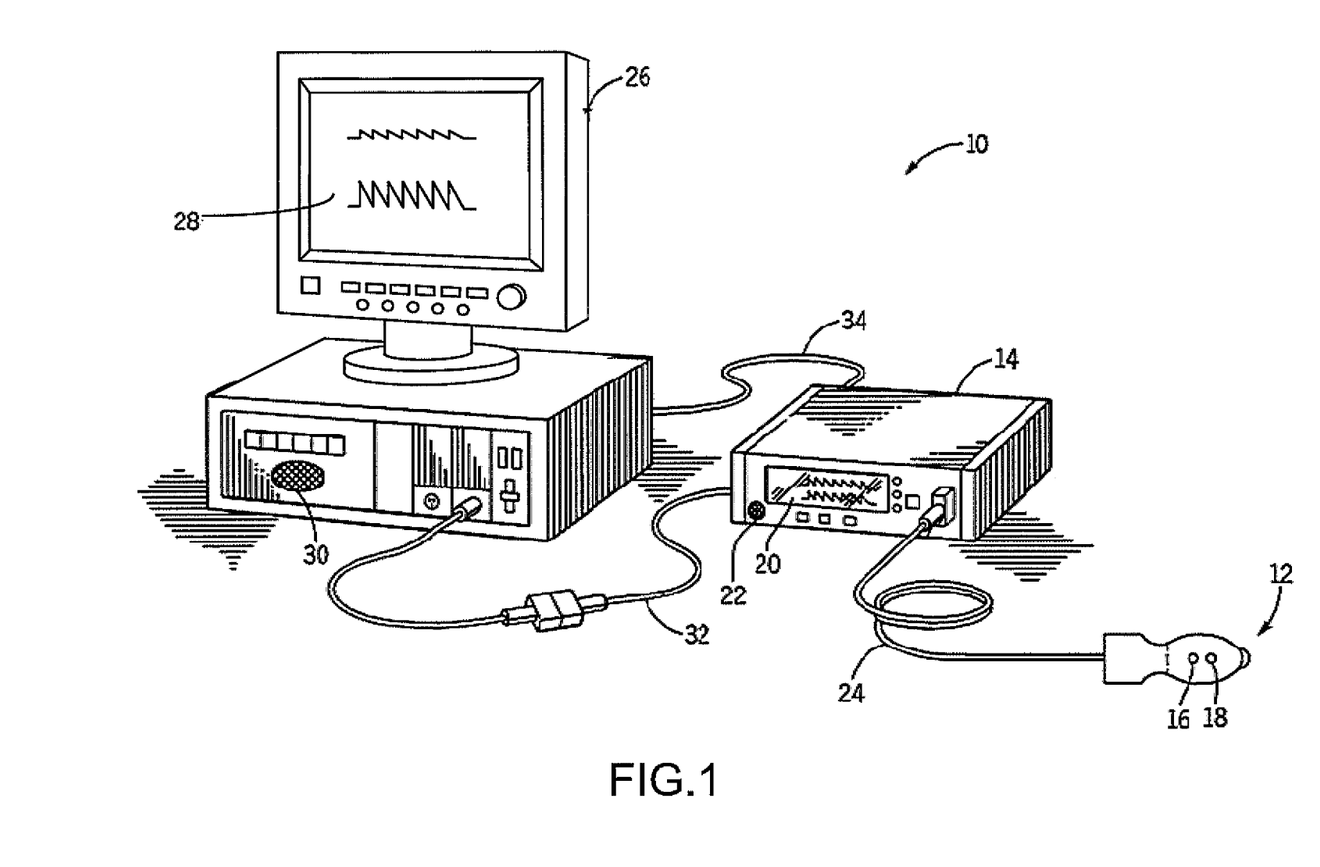
FIG. 1 is a perspective view of a pulse oximetry system.

FIG. 1 is a perspective view of an embodiment of a pulse oximetry system 10. The system 10 includes a sensor 12 and a pulse oximetry monitor 14. The sensor 12 includes an emitter 16 for emitting light at two or more wavelengths into a patient's tissue. A detector 18 is also provided in the sensor 12 for detecting the light originally from the emitter 16 that emanates from the patient's tissue after passing through the tissue. The emitter 16 and detector 18 may be on opposite sides of a digit such as a finger or toe, in which case the light that is emanating from the tissue has passed completely through the digit. In an embodiment the emitter 16 and detector 18 may be arranged so that light from the emitter 16 penetrates the tissue and is reflected by the tissue into the detector 18, such as a sensor designed to obtain pulse oximetry data from a patient's forehead.

In an embodiment, the sensor may be connected to and draw its power from the monitor 14 as shown. In another embodiment, the sensor may be wirelessly connected to the monitor 14 and include its own battery or similar power supply (not shown). The monitor 14 may be configured to calculate physiological parameters based on data received from the sensor 12 relating to light emission and detection. Further, the monitor 14 includes a display 20 configured to display the physiological parameters, other information about the system, and/or alarm indications. In the embodiment shown, the monitor 14 also includes a speaker 22 to provide an audible alarm in the event that the patient's physiological parameters are not within a normal range, as defined based on patient characteristics.

In an embodiment, the sensor 12 is communicatively coupled to the monitor 14 via a cable 24. However, in other embodiments a wireless transmission device (not shown) or the like may be utilized instead of or in addition to the cable 24.

In the illustrated embodiment, the pulse oximetry system 10 also includes a multi-parameter patient monitor 26. The monitor may be cathode ray tube type, a flat panel display (as shown) such as a liquid crystal display (LCD) or a plasma display, or any other type of monitor now known or later developed. The multi-parameter patient monitor 26 may be configured to calculate physiological parameters and to provide a central display 28 for information from the monitor 14 and from other medical monitoring devices or systems (not shown). For example, the multiparameter patient monitor 26 may be configured to display an estimate of a patient's blood oxygen saturation generated by the pulse oximetry monitor 14 (referred to as an "$SpO_2$" measurement), pulse rate information from the monitor 14 and blood pressure from a blood pressure monitor (not shown) on the display 28. Additionally, the multi-parameter patient monitor 26 may emit a visible or audible alarm via the display 28 or a speaker 30, respectively, if the patient's physiological parameters are found to be outside of the normal range.

The monitor 14 may be communicatively coupled to the multi-parameter patient monitor 26 via a cable 32 or 34 coupled to a sensor input port or a digital communications port, respectively and/or may communicate wirelessly (not shown). In addition, the monitor 14 and/or the multi-parameter patient monitor 26 may be connected to a network to enable the sharing of information with servers or other workstations (not shown). The monitor 14 may be powered by a battery (not shown) or by a conventional power source such as a wall outlet.

Figure 2:
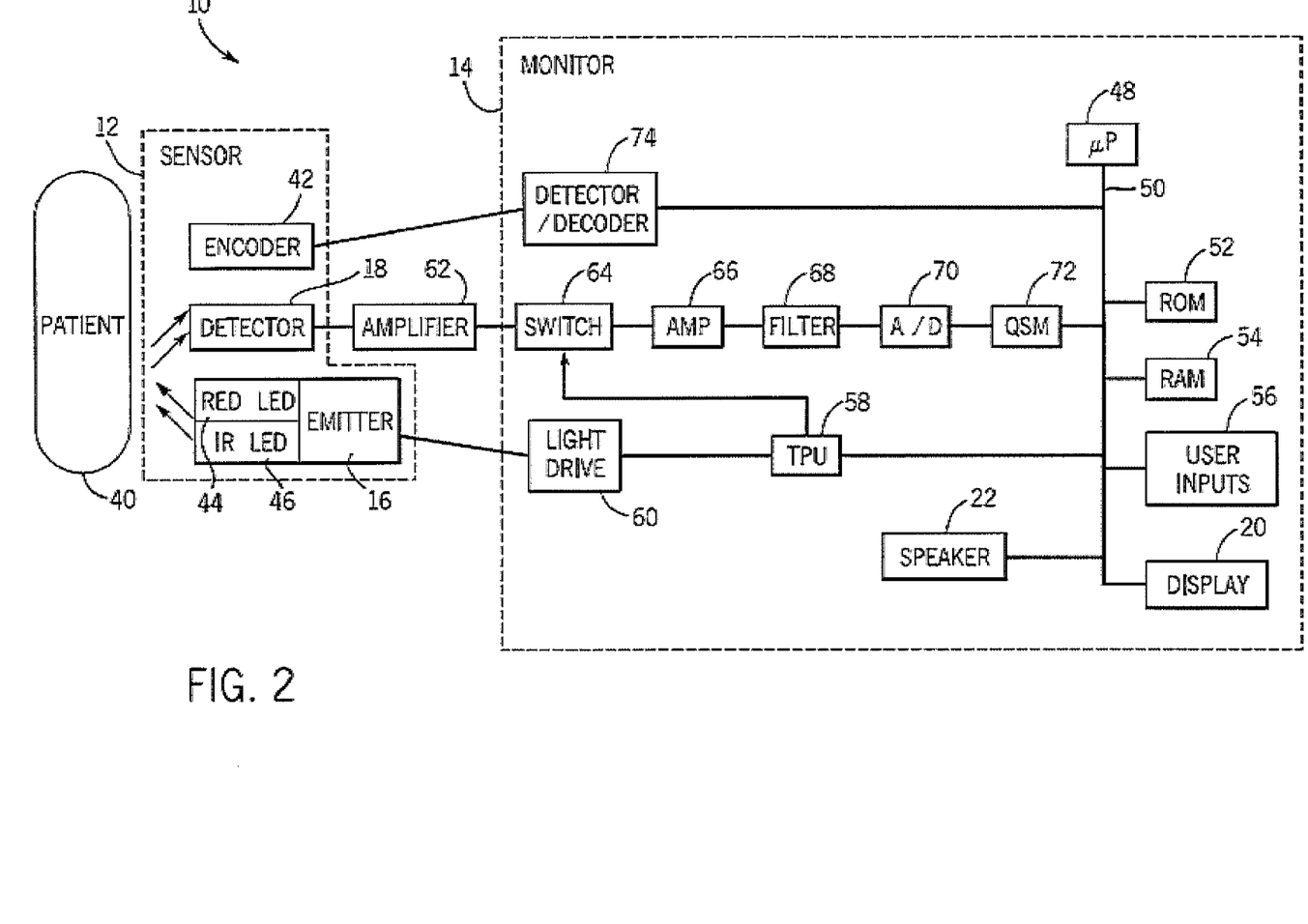
FIG. 2 is a block diagram of the exemplary pulse oximetry system of FIG. 1 coupled to a patient.

FIG. 2 is a block diagram of the embodiment of a pulse oximetry system 10 of FIG. 1 coupled to a patient 40 in accordance with present embodiments. Specifically, certain components of the sensor 12 and the monitor 14 are illustrated in FIG. 2. The sensor 12 includes the emitter 16, the detector 18, and an encoder 42. In the embodiment shown, the emitter 16 is configured to emit at least two wavelengths of light, e.g., RED and IR, into a patient's tissue 40. Hence, the emitter 16 may include a RED light emitting light source such as the RED light emitting diode (LED) 44 shown and an IR light emitting light source such as the IR LED 46 shown for emitting light into the patient's tissue 40 at the wavelengths used to calculate the patient's physiological parameters. In certain embodiments, the RED wavelength may be between about 600 nm and about 700 nm, and the IR wavelength may be between about 800 nm and about 1000 nm.

It should be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein light may also include any wavelength within the radio, microwave, infrared, visible, ultraviolet, or X-ray spectra, and that any suitable wavelength of electromagnetic radiation may be appropriate for use with the present techniques. Similarly, detector 18 may be chosen to be specifically sensitive to the chosen targeted energy spectrum of the light source 16.

In an embodiment, the detector 18 may be configured to detect the intensity of light at the RED and IR wavelengths. In operation, light enters the detector 18 after passing through the patient's tissue 40. The detector 18 converts the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, the detector 18 sends the signal to the monitor 14, where physiological parameters may be calculated based on the absorption of the RED and IR wavelengths in the patient's tissue 40. An example of a device configured to perform such calculations is the Model N600x pulse oximeter available from Nellcor Puritan Bennett LLC.

In an embodiment, the encoder 42 may contain information about the sensor 12, such as what type of sensor it is (e.g., whether the sensor is intended for placement on a forehead or digit) and the wavelengths of light emitted by the emitter 16. This information may be used by the monitor 14 to select appropriate algorithms, lookup tables and/or calibration coefficients stored in the monitor 14 for calculating the patient's physiological parameters.

In addition, the encoder 42 may contain information specific to the patient 40, such as, for example, the patient's age, weight, and diagnosis. This information may allow the monitor 14 to determine patient-specific threshold ranges in which the patient's physiological parameter measurements should fall and to enable or disable additional physiological parameter algorithms. The encoder 42 may, for instance, be a coded resistor which stores values corresponding to the type of the sensor 12, the wavelengths of light emitted by the emitter 16, and/or the patient's characteristics. These coded values may be communicated to the monitor 14, which determines how to calculate the patient's physiological parameters and alarm threshold ranges. In another embodiment, the encoder 42 may include a memory on which one or more of the following information may be stored for communication to the monitor 14: the type of the sensor 12; the wavelengths of light emitted by the emitter 16; the proper calibration coefficients and/or algorithms to be used for calculating the patient's physiological parameters and/or alarm threshold values; the patient characteristics to be used for calculating the alarm threshold values; and the patient-specific threshold values to be used for monitoring the physiological parameters.

In an embodiment, signals from the detector 18 and the encoder 42 may be transmitted to the monitor 14. In the embodiment shown, the monitor 14 includes a general-purpose microprocessor 48 connected to an internal bus 50. The microprocessor 48 is adapted to execute software, which may include an operating system and one or more applications, as part of performing the functions described herein. Also connected to the bus 50 are a read-only memory (ROM) 52, a random access memory (RAM) 54, user inputs 56, the display 20, and the speaker 22.

The RAM 54 and ROM 52 are illustrated by way of example, and not limitation. Any computer-readable media may be used in the system for data storage. Computer-readable media are capable of storing information that can be interpreted by the microprocessor 48. This information may be data or may take the form of computer-executable instructions, such as software applications, that cause the microprocessor to perform certain functions and/or computer-implemented methods. Depending on the embodiment, such computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 provides timing control signals to a light drive circuitry 60 which controls when the emitter 16 is illuminated and multiplexed timing for the RED LED 44 and the IR LED 46. The TPU 58 also controls the gating-in of signals from detector 18 through an amplifier 62 and a switching circuit 64. These signals are sampled at the proper time, depending upon which light source is illuminated. The received signal from the detector 18 may be passed through an amplifier 66, a low pass filter 68, and an analog-to-digital converter 70. The digital data may then be stored in a queued serial module (QSM) 72 (or buffer) for later downloading to the RAM 54 as the QSM 72 fills up. In one embodiment, there may be multiple separate parallel paths having the amplifier 66, the filter 68, and the A/D converter 70 for multiple light wavelengths or spectra received.

In an embodiment, the microprocessor 48 may determine the patient's physiological parameters, such as $SpO_2$ and pulse rate, using various algorithms and/or look-up tables based on the value of the received signals and/or data corresponding to the light received by the detector 18. Signals corresponding to information about the patient 40, and particularly about the intensity of light emanating from a patient's tissue over time, may be transmitted from the encoder 42 to a decoder 74. These signals may include, for example, encoded information relating to patient characteristics. The decoder 74 may translate these signals to enable the microprocessor to determine the thresholds based on algorithms or look-up tables stored in the ROM 52. The encoder 42 may also contain the patient-specific alarm thresholds, for example, if the alarm values are determined on a workstation separate from the monitor 14. The user inputs 56 may also be used to enter information about the patient, such as age, weight, height, diagnosis, medications, treatments, and so forth. In certain embodiments, the display 20 may exhibit a list of values which may generally apply to the patient, such as, for example, age ranges or medication families, which the user may select using the user inputs 56. The microprocessor 48 may then determine the proper thresholds using the user input data and algorithms stored in the ROM 52. The patient-specific thresholds may be stored on the RAM 54 for comparison to measured physiological parameters.

The embodiments described herein relate to determining one or more statistical parameters of data from which an estimated physiological parameter value has been determined. Statistical parameters associated with the physiological parameter include parameters related to the accuracy of the estimated value such as error estimates and probability distributions of the data.

Figure 3:
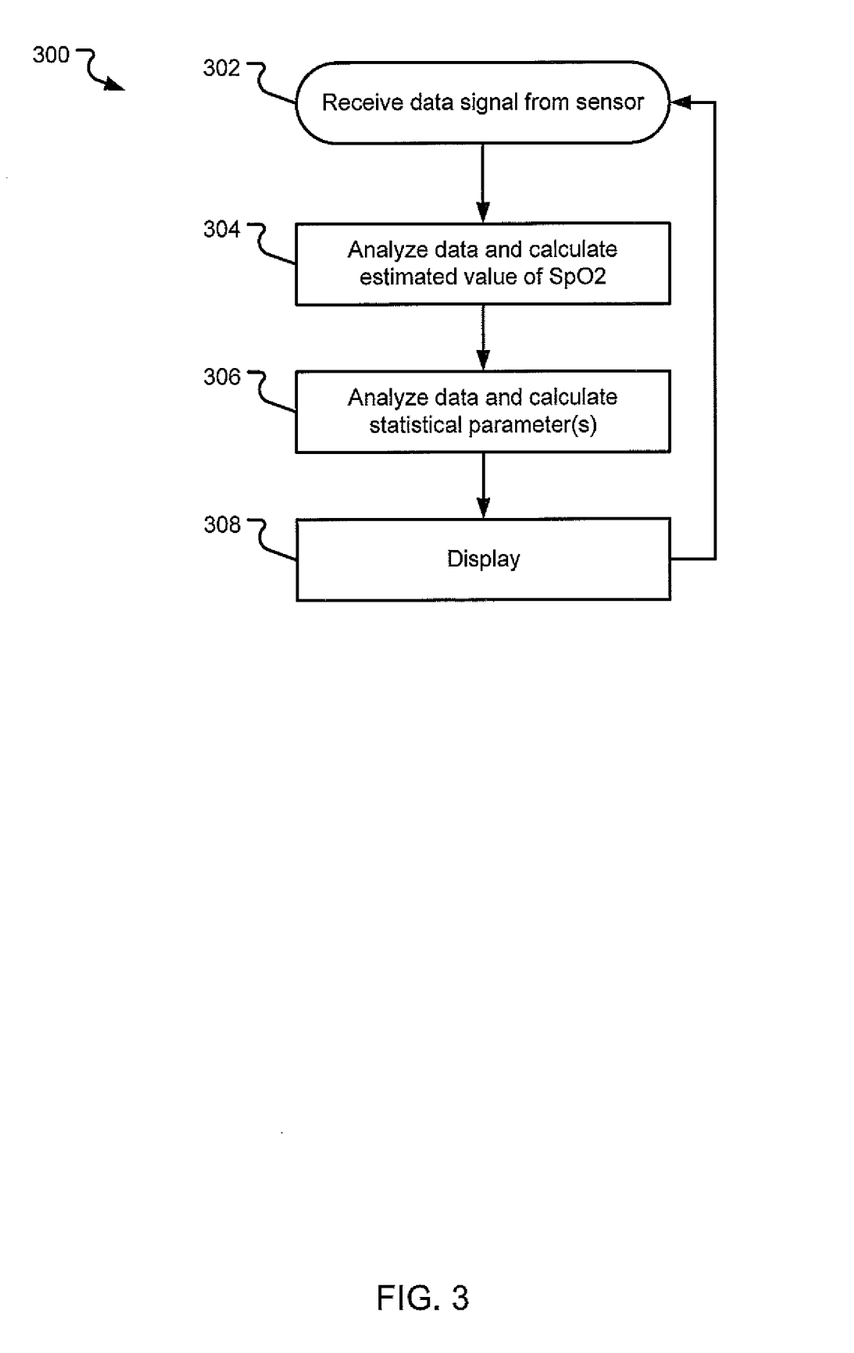
FIG. 3 illustrates an embodiment of a method for determining and displaying a statistical parameter indicative of the accuracy of an estimated physiological parameter.

FIG. 3 illustrates an embodiment of a method for determining and displaying a statistical parameter indicative of the accuracy of an estimated physiological parameter. In the method 300, information and/or data are received from a data source in a receive data operation 302. In the context of the pulse oximeter described above, the receive data operation 302 includes receiving an electronic signal from a sensor indicative of the light received by the detector and processing that signal to generate data that can be processed by the microprocessor. In an embodiment, the data, or samples thereof, may be temporarily stored in a buffer to allow multiple analyses of the same data. In additional, some or all of the data may be retained for some period of time for subsequent processing at a later time.

In an embodiment, the received data are analyzed to generate an estimated value of the physiological parameter that is being measured in the generate estimate operation 304. In the context of a pulse oximeter, one physiological parameter estimated is the oxygen saturation of the blood of the patient. In an embodiment, the oxygen saturation of the patient's blood is calculated based on the most recent data received from the sensor in order to provide a current measurement of the oxygen saturation. The estimated value of the oxygen saturation may be generated by a sophisticated algorithm and may utilize a significant amount of processor cycles and signal processing hardware (e.g., filters, amplifiers, high-resolution digital to analog converters, etc.). In an embodiment, generation of the estimated value of the oxygen saturation may use statistical information derived from data in the generation of the final estimate. An example of generating an estimated value for oxygen saturation is described in the commonly-assigned U.S. Pat. No. 6,836,679, titled "Method and apparatus for estimating physiological parameters using model-based adaptive filtering". Other methods for generating the estimated value are known in the art and any suitable method, now known or later developed, may be used.

In an embodiment, in addition to the generation of the estimated value, one or more statistical parameters describing the data are calculated in a calculate statistical parameters operation 306. In the embodiment shown, the calculate statistical parameters operation 306 is performed after the generate estimate operation 304. In embodiments, the statistical parameter(s) may be calculated before, concurrently with or as part of the generate estimate operation 304. Furthermore, the statistical parameter(s) calculated may or may not be used in the calculation of the estimated value and may or may not be calculated by the same module, software application or component of the pulse oximeter that calculates the estimated value. For example, in an embodiment, a single software application may be utilized to calculate all parameters. In another embodiment separate and independent software modules or system components may be used to calculate each parameter described herein.

One statistical parameter that may be determined from the data is a single value representing the accuracy of the estimated value. Accuracy is a well known statistical term of art referring how close an estimated value is likely to be to the actual value based on the errors and limitations of the measurement process and the data obtained. Accuracy can be quantified by many different techniques, including reporting a single value that is a numerical representation of the accuracy of the estimated value. For example, the accuracy of an estimated value of oxygen saturation may be determined by calculating a standard deviation of the physiological data from which the estimated value is determined; the smaller the standard deviation, the greater the accuracy of the estimated value. Thus, the standard deviation itself may be displayed as a parameter representing the accuracy of the estimated value.

In an embodiment, the accuracy of an estimated value may be further determined by more complicated calculations involving a detailed analysis of data received from the sensor. A number of data characteristics potentially indicative of the accuracy of pulse oximetry calculations are known to those skilled in the art. Examples include pulse amplitude, pulse shape, correlation of the IR and RED photoplethysmograph, as well as temporal variations in any of these characteristics. Those skilled in the art of pulse oximeter design will also recognize that multiple data characteristics may be combined empirically in order to more accurately reflect the accuracy of a pulse oximetry system under challenging conditions that may be created experimentally or encountered in clinical usage. Those skilled in the art will also recognize that in order to design such an empirical combination, the accuracy of oxygen saturation and pulse rate measurements under challenging conditions may be independently assessed by techniques such as arterial blood sampling, ECG monitoring, or use of a second pulse oximeter at a different tissue site.

In embodiments, statistical parameters calculated in the calculate statistical parameters operation 306 may also include parameters based on probability distribution of the data. One such statistical parameter is a confidence interval. A confidence interval is an interval estimate of a parameter. The confidence interval represents a range of values within which the actual value of the parameter is expected to be to known probability, referred to as the confidence level. For example, a confidence interval may be a range within which the actual value is expected to be with a 95% certainty. An alternative way of stating this is that there is a 95% probability that the actual value will be within the confidence interval.

In an embodiment, when calculating confidence intervals, the confidence level to be used is identified as part of the operation 306. The confidence level may be predetermined by the system manufacturer, selected automatically by the system, or may be adjustable by the user of the system. For example, in an embodiment a system may use a 95% confidence level for all confidence interval calculations unless a user has specifically selected a different confidence level. The system may facilitate user selection of confidence levels by providing an interface, such as a confidence level selection menu, through which the user can select a confidence level (e.g., 90%, 95%, 98%, etc.) or enter a user designated confidence level. Confidence levels received by the system from a user through such an interface may be stored in memory on the system and also may be displayed on the display GUI as described in greater detail below.

In an embodiment, confidence intervals may also be represented as confidence limits, such as an upper confidence limit and a lower confidence limit. A confidence limit is an interval estimate of a parameter indicating the probability that the actual value is above (or below) the limit. For the purposes of this disclosure, the terms "upper confidence limit" or "upper limit" refers to the upper limit of any confidence interval (including a confidence interval with no lower limit) and, likewise, the term "lower confidence limit" will be used when referring to the lower limit of any confidence interval with a lower limit. The relationship between the estimated value, its accuracy estimate, and its confidence interval depends on the probability distribution function of the measurement errors. Measurement errors are often presumed to have a Gaussian probability distribution, characterized by the "bell-curve" function $e^{-(x/\sigma)^2}$, where $\sigma$ denotes the standard deviation of the measurement errors (i.e. the accuracy). Assuming a Gaussian error distribution, an oxygen saturation estimate of 92% with an accuracy, $\sigma$, of 3% will have a 95% confidence interval of 92%±6%, or 86%-98%, because 95% of the area under the curve defined by a Guassian error distribution falls within the range of ±2$\sigma$.

Confidence intervals, confidence limits and accuracy calculations are examples of statistical parameters that may be calculated by the method 300. The reader will understand that any other statistical parameter related to any aspect of the data (e.g., signal strength, noise, harinonics, etc.) may be calculated as part of the calculate statistical parameter operation 306.

In an embodiment, after the calculations have been made, a display operation 308 is performed. In the display operation 308, the estimated value of the SpO$_2$ may be displayed to a user of the pulse oximeter system, such as a doctor, nurse, other caregiver, or patient. The display may be numerical, graphical or a combination of both in nature. For example, in an embodiment the system generates a graphical user interface (GUI) that is presented on a monitor or other display device that includes some graphical element such as an arrow that indicates the estimated value.

The display operation 308 may also include displaying one or more of the calculated statistical parameters. In an embodiment, the operation 308 simultaneously depicts the estimated value and a representation of the probability that the physiological parameter is above or below one or more confidence limits. In situations in which the parameter has both high and low alarm limits, a decision to display probability of being above or below a given value may be based on which alarm limit each value is closest to. This conveys not only changes in accuracy of the estimated value over time, but also gives the clinician an intuitive depiction of what said changes in accuracy might mean.

In an embodiment, the method 300 is performed continuously, which is illustrated by the flow returning to the receive data operation 302. That is, data is continually being received, calculations are made from the most recent data and the displayed values are continuously updated. Depending on the implementation, this can be done in a true continuous process or can be done by periodically repeating the operations in FIG. 3 for batches of data received and revising the displayed values after each repetition.

Figure 4:
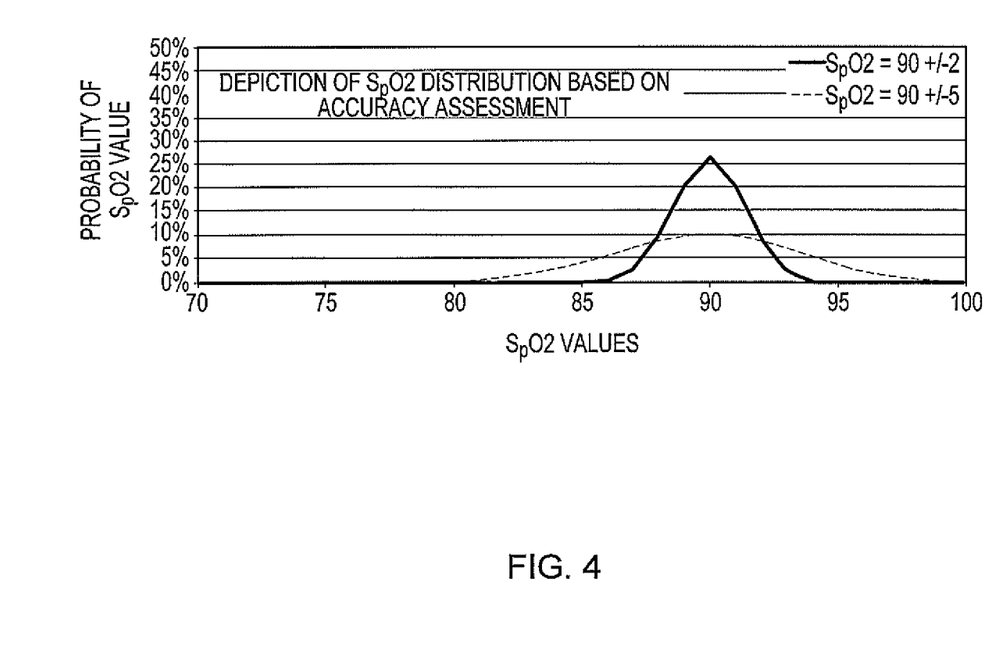
FIG. 4 shows a depiction of two Gaussian bell-curves of the probability distribution in which the estimated $SpO_2$ value is 90%, but having accuracies of ±2 (solid) and ±5 (dashed) respectively.

FIG. 4 shows a depiction of two Gaussian bell-curves of the probability distribution in which the estimated SpO$_2$ value is 90%, but having accuracies of ±2% (solid) and ±5% (dashed) respectively. As shown in FIG. 4, the difference in accuracy has a large effect on the probability distribution and the probability that the actual SpO$_2$ value is above or below any particular value. For example, if the accuracy is ±2%, there is nearly a 100% chance that the actual value of the SpO$_2$ value is within the interval of 85% to 95%. The same can not be said of the data having an accuracy of ±5%.

Figure 5:
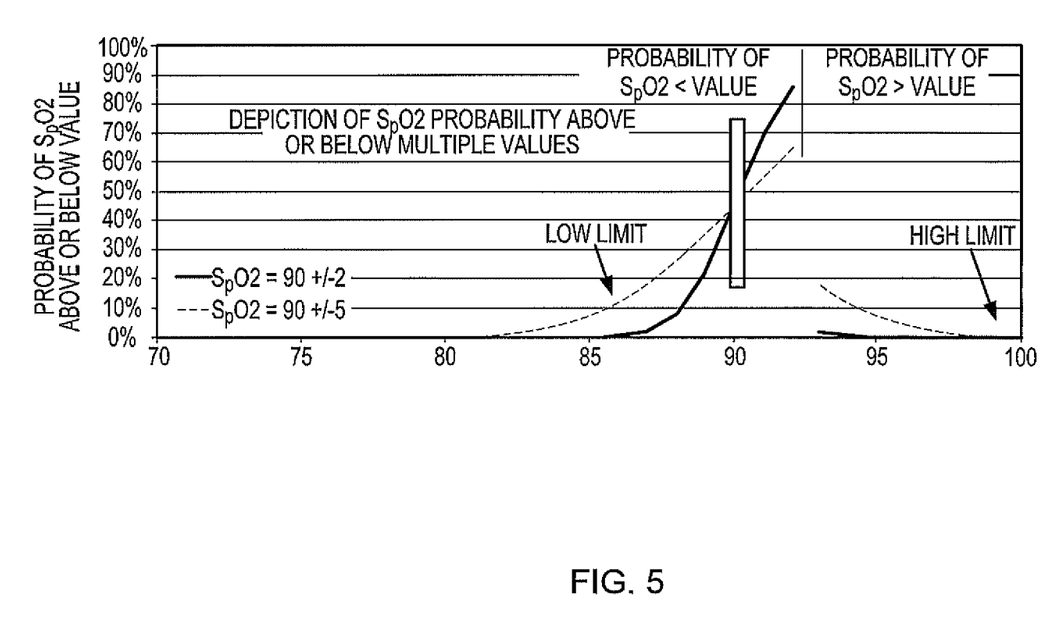
FIG. 5 depicts the same distributions as shown in FIG. 4 plotted as the cumulative probability that the actual $SpO_2$ value is below or above each of the $SpO_2$ values on x-axis.

FIG. 5 depicts the same two contrasting examples, but shows the cumulative probability that the actual SpO$_2$ value is below or above each of the SpO$_2$ values on x-axis. For convenience, only a portion of two different sets of curves are displayed on FIG. 5. Midway between the high limit (100% saturation) and low limit (85% saturation), the curves switch from "probability of SpO$_2$ below value" curves at each accuracy to "probability of SpO$_2$ above value" curves at each accuracy. If all of the "probability of SpO$_2$ below value" curves were displayed, they would start to level off and end at the point 100% probability/100% saturation. The "probability of SpO$_2$ above value" curves would be seen to continue to rise and then level off, approaching 100% probability to end at the point 100% probability/0% saturation. It should also be pointed out that at the SpO$_2$ value of 90% the "above" and "below" curves converge.

Figure 6:
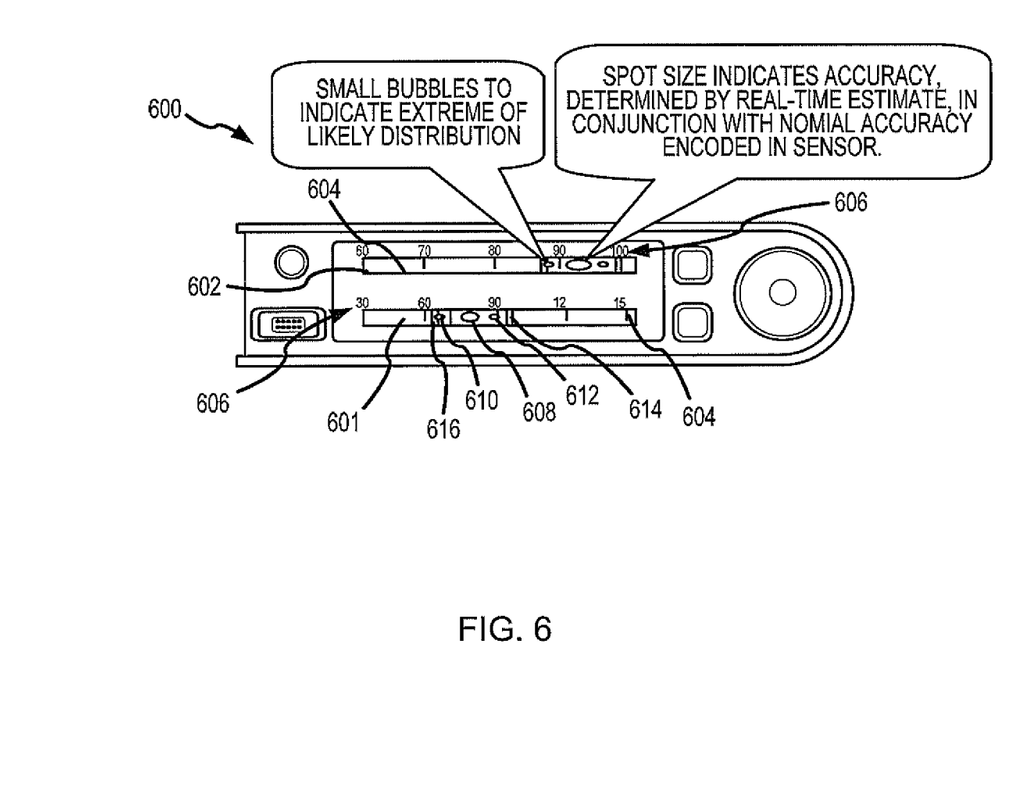
FIG. 6 is an embodiment of a graphical user interface (GUD depicting a "carpenter's level" graphic showing the probability distribution information for an estimated physiological parameter.
Figure 7:
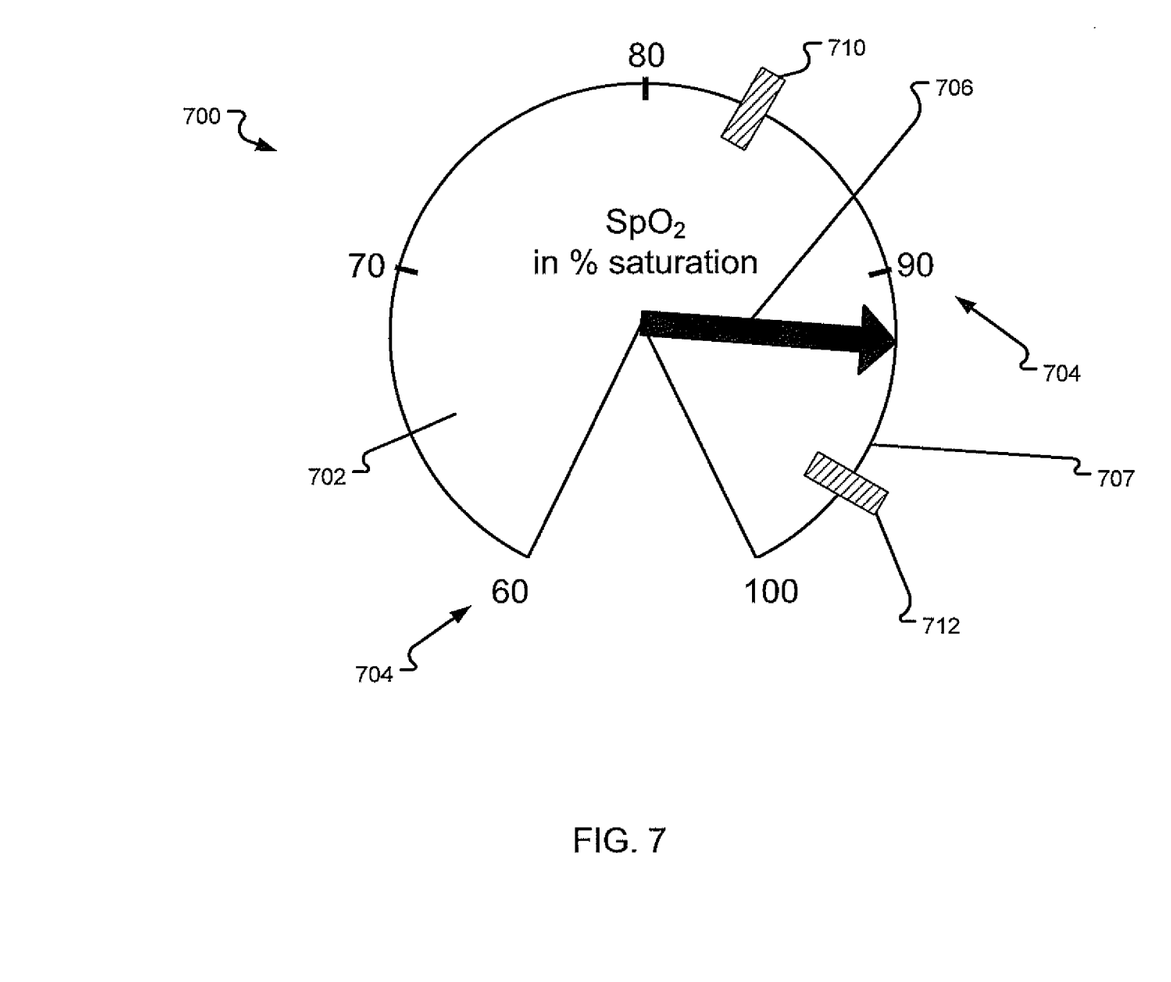
FIG. 7 is another embodiment of a GUI depicting a radial display, in which the estimated value of the physiologic parameter is indicated by the arrow and probability distribution information is displayed along a circumference of the radial display.
Figure 8:
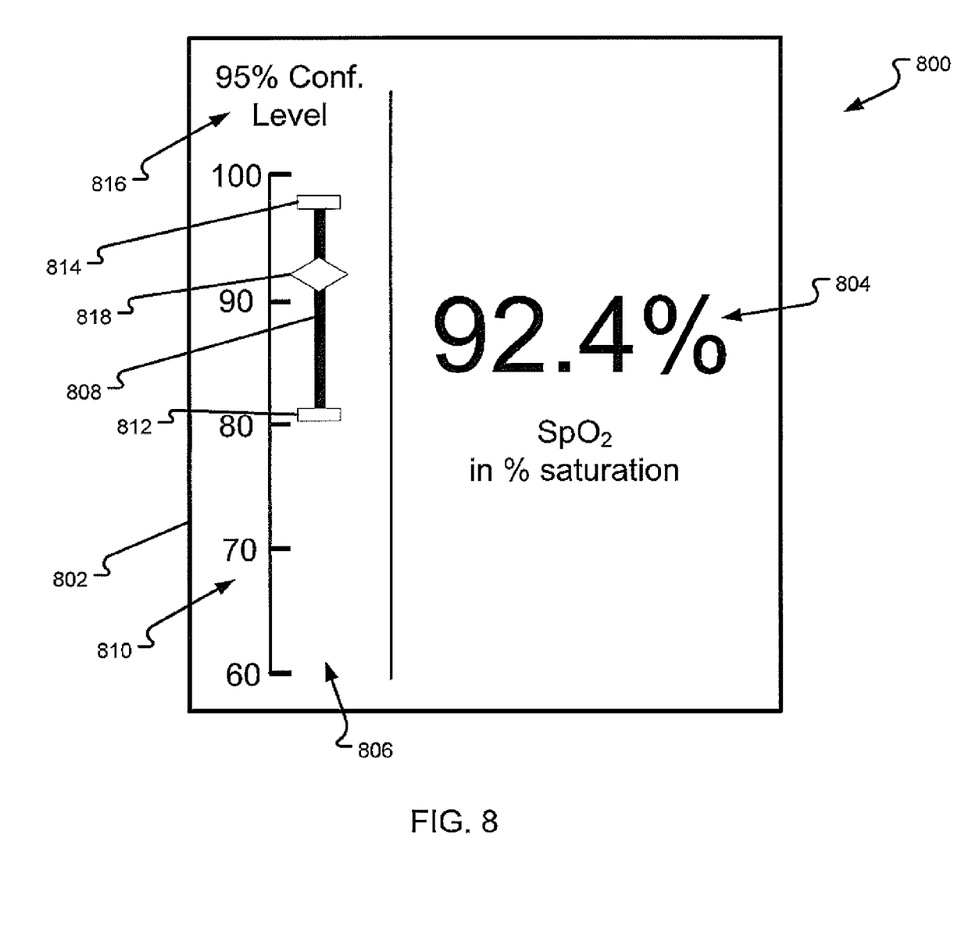
FIG. 8 is another embodiment of a GUI depicting a combination of a numerical parameter display and graphical display of the estimated value and the statistical parameters.

FIGS. 6-8 illustrate several different embodiments of GUIs for displaying the statistical parameters shown in FIGS. 4 and 5. FIG. 6 is an embodiment of a GUI depicting a "carpenter's level" graphic showing the probability distribution information for an estimated physiological parameter. In the embodiment shown, the GUI 600 includes two displays 601, 602, each including a bar 604 associated with a scale 606. The embodiment is a pulse oximeter GUI and the upper scale 606 is in percent saturation, while the lower display 601 indicates the pulse rate of the patient.

The GUI 600 displays the estimated value for the physiological parameter, the confidence interval for the estimated value, the accuracy of the estimated value and any alarm thresholds that, if exceeded (i.e., the estimated value goes above an upper alarm threshold or below a lower alarm threshold), would result in an alarm being generated by the oximeter.

In the embodiment shown, the estimated value of the physiological parameter is indicated by an ellipsoid 608 located on the bar 604 and centered under the estimated value on the bar's associated scale 606. For example, in FIG. 6 the estimated value for the SpO$_2$ is approximately 93% saturation and the estimated pulse is 80 beats per minute. The accuracy is indicated by the width of the ellipsoid 608; a wider ellipsoid indicates a less accurate estimate and a smaller ellipsoid indicates a more accurate estimate. The statistical parameter used for the accuracy may be the standard deviation of the data or some other calculated statistical parameter that is a single value representation of the accuracy of the estimate as described above.

The confidence interval is displayed through the use of two smaller ellipsoids 610, 612. One ellipsoid 610 is located at a lower confidence limit of the confidence interval while the other ellipsoid 612 is located at an upper confidence limit. For example, in FIG. 6 the lower confidence limit of the SpO$_2$ estimate is approximately 88% saturation and the upper confidence limit is approximately 97% saturation.

FIG. 6 further illustrates an upper alarm threshold indicator 614 and a lower alarm threshold indicator 616 on each display 601, 602. These take the form of rectangles 614, 616 in the bar 602 that bound an interval of acceptable values for the physiological parameter being measured. In an embodiment, this interval may be displayed in a different color, such as green, than the bar 602, in order to more readily identify the acceptable interval.

FIG. 7 is another embodiment of a GUI depicting a radial display, in which the estimated value of the physiologic parameter is indicated by the arrow. In this embodiment, the GUI 700 takes the form of a dial 702 with a scale 704 around the circumference of the dial 702. An arrow 706 points to the location on the scale 704 that corresponds to the current estimated value of the parameter being measured. The real-time accuracy estimate may be quantitatively depicted by the width of the arrow 706 (as shown), by error bars near the tip of the arrow (not shown), or by varying the pattern, gray-scale or color of the arrow across its width, such as with a quantitative legend near an edge of the graphic to assist with interpreting the accuracy indication. These are just a few examples of different features of the arrow 706 that could be varied or otherwise used to indicate accuracy.

In addition, two confidence limit markers 710, 712 are also provided on the GUI 700 to indicate to the clinician information concerning the accuracy and confidence intervals associated with the estimated value. The GUI 700 includes a lower confidence limit mark 710 on the circumference at a position corresponding to the value of the lower confidence limit. The GUI 700 further includes an upper confidence limit mark 712 on the circumference of the dial 702 at a position corresponding to the value of the upper confidence limit. Although not shown, markers or other indicators of the alarm thresholds could also be indicated. For example, a green pie-shaped region (not shown) could be provided to indicate the non-alarm region based on the alarm thresholds.

FIG. 8 is another embodiment of a GUI depicting a combination of a numerical parameter display and graphical display of the estimated value and the statistical parameters. In this embodiment the GUI 800 takes the form of a display area 802 containing a numerical display 804 next to a graphical display 806. The numerical display 804 shows the estimated value of the measured parameter. The graphical display 806 graphically shows the estimated value for the physiological parameter, the confidence limits and the accuracy of the estimated value.

In the embodiment shown, on the graphical display 806, the confidence interval is displayed as a bar 808 next to a scale 810 in which the current estimated value of SpO2 is graphically illustrated by the location of the estimated value marker 818 relative to the scale 810 and the extent of the bar 808 relative to the scale 810 indicates the confidence interval. Independent confidence limits may also be shown such as by the markers 812, 814 as illustrated. For example, in FIG. 8 the estimated value for the $SpO_2$ is approximately 92.4% saturation, the 95% confidence interval 808 extends from about 98% to 81% saturation (i.e., there is a 95% confidence that the actual $SpO_2$ value is within this interval), the upper confidence limit is about 98% saturation (i.e., there is a 95% confidence the actual value of SpO2 is less than 98% saturation) and the lower confidence limit is about 81%.

In the embodiment shown, the accuracy is indicated by the size of the estimated value marker 818 on the confidence interval bar 808. In an embodiment, a wider marker 818 indicates a less accurate estimate and a smaller marker 818 indicates a more accurate estimate. In an embodiment, different features may be altered rather than size of the marker 818 as described above.

The embodiments described above illustrate several different examples of GUIs that display statistical parameters related to the accuracy of estimated physiological parameters. Other methods of displaying this information will immediately be suggested to the reader and are within the scope of this disclosure. For example, in embodiments the accuracy or other statistical parameter(s) of an estimated physiological parameter may be quantitatively depicted by varying a characteristic of the font in which its value is displayed, such as its thickness, orientation, size, or color. Furthermore, the statistical parameter may be depicted in a trend plot along with a trend of the physiological parameter. As yet another example, the same information could be portrayed in either portrait or landscape orientation.

It will be apparent to those skilled in the art of medical monitoring that the utility of these accuracy depictions is not limited to a real-time display. For example, doctors who review physiological data that have been previously collected and uploaded to a Hospital Information System may wish to simultaneously view a depiction the accuracy of said data, on their PC, PDA or other display device.

Figure 9:
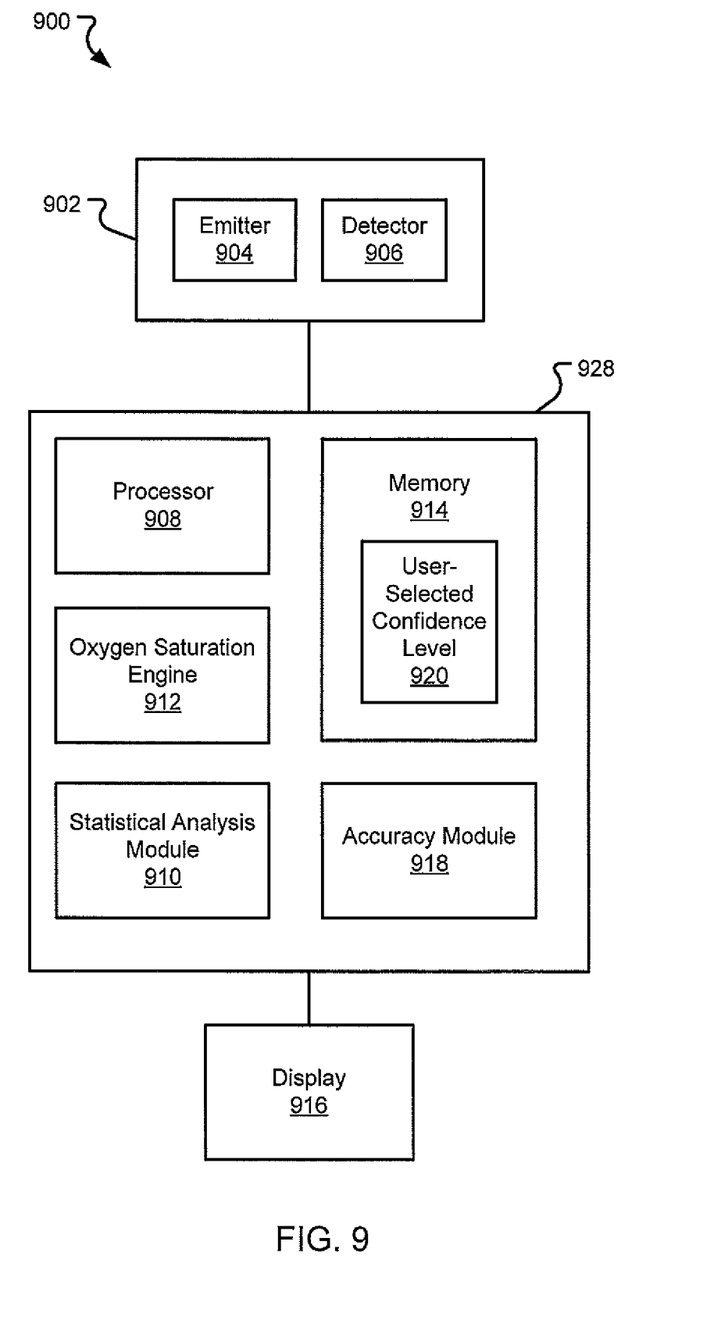
FIG. 9 is a block diagram illustrating some of the components of a pulse oximetry system that simultaneously displays an estimated oxygen saturation value and statistical parameters conveying information about the accuracy of the estimated value.

FIG. 9 is a block diagram illustrating some of the components of a pulse oximetry system that simultaneously displays an estimated oxygen saturation value and one or more statistical parameters conveying information about the accuracy of the estimated value. In the embodiment shown, the system 900 includes a sensor 902 containing a light emitter 904 and a light detector 906; and, in a separate housing 928, a processor 908, a statistical analysis module 910; an oxygen saturation engine 912; an accuracy module 918 and a memory 914. A display 916 is also provided. The sensor 902 and its components operate as described previously with reference to FIG. 2.

The memory 914 may include RAM, flash memory or hard disk data storage devices. The memory stores data, which may be filtered or unfiltered data, received from the detector 906. The data may be decimated, compressed or otherwise modified prior to storing in the memory 914 in order to increase the time over which data may be retained. In addition, the memory 914 may also store one or more predetermined confidence levels including any user-selected confidence levels 920 for use by the statistical analysis module 910 when calculating a confidence limit or confidence interval.

The oxygen saturation engine 912 generates a current oxygen saturation measurement from the data generated by the sensor. The statistical analysis module 910 performs the analyses of the data and calculates the statistical parameter(s) for display with the estimated value of the oxygen saturation. In an embodiment, the statistical analysis module is capable of calculating one or more parameters such as an upper confidence limit, a lower confidence limit, and a confidence interval based on information received from the sensor and a stored confidence level.

In the embodiment shown, a separate accuracy module 918 is illustrated. The accuracy module 918 is capable of calculating the accuracy of the estimated value of the oxygen saturation. This accuracy may then be displayed to the user via a user interface presented on the display 916.

In an embodiment, the oxygen saturation engine 912, statistical analysis module 910 and accuracy module 918 may each be a dedicated hardware circuit that may include filters, firmware comprising lookup tables or other data, and its own processor (not shown) that allow it to generate the current oxygen saturation measurement. In an embodiment, they may be implemented as a single software application or separate software applications that are executed, in whole or in part, by the system processor 908. In yet another embodiment functions described herein as being performed by the oxygen saturation engine and modules may be distributed among hardware, software and firmware throughout the system 900 and its other components.

The display 916 may be any device that is capable of generating an audible or visual notification. The display need not be integrated into the other components of the system 900 and could be a wireless device or even a monitor on a general purpose computing device (not shown) that receives email or other transmitted notifications from the oximeter 900. The audible portion of the display 916 may also be used to convey a determination of the accuracy of the measured physiological parameters, by modifying either an alarm tone or a once-per-pulse beep, wherein the modification is proportional to the determined accuracy. In cases where the audible notification conveys a once-per-pulse beep wherein the pitch of the beep indicates the oxygen saturation, the audible representation of accuracy may modify some other aspect of the beep tone. Examples of audible modifications that may intuitively convey changes in accuracy include simultaneously emitting two or more closely spaced pitches in place of a single pitch (akin to an increasingly out-of-tune note on a piano), inducing rapid variations in the pitch or amplitude of a tone (akin to vibrato in the voice and many instruments), as well as changes in timbre.

It will be clear that the described systems and methods are well adapted to attain the ends and advantages mentioned as well as those inherent therein. Those skilled in the art will recognize that the methods and systems described within this specification may be implemented in many different manners and as such are not to be limited by the foregoing exemplified embodiments and examples. In other words, functional elements being performed by a single or multiple components, in various combinations of hardware and software, and individual functions can be distributed among software applications and even different hardware platforms. In this regard, any number of the features of the different embodiments described herein may be combined into one single embodiment and alternate embodiments having fewer than or more than all of the features herein described are possible.

While various embodiments have been described for purposes of this disclosure, various changes and modifications may be made which are well within the scope of the described technology. Numerous other changes may be made which will readily suggest themselves to those skilled in the art and which are encompassed in the spirit of the disclosure and as defined in the appended claims.

What is claimed is:

1. A method for displaying oxygen saturation of a patient's blood comprising, using a processor configured to determine the oxygen saturation, wherein the processor is associated with a patient monitor, and wherein determining the oxygen saturation comprises:
    calculating using the processor an estimated value of the oxygen saturation of the patient's blood based at least in part upon information received from a sensor;
    displaying the estimated value on a display of the patient monitor;
    calculating, using the processor, at least one statistical parameter associated with the estimated value based at least in part upon information received from the sensor, wherein calculating the at least one statistical parameter comprises calculating an accuracy of the estimated value based at least in part upon one or more data characteristics of the information received from the sensor, wherein the one or more data characteristics comprise a pulse amplitude, a pulse shape, or a correlation of infrared and red components; and
    displaying the at least one statistical parameter with the estimated value on the display, wherein displaying the at least one statistical parameter comprises displaying the accuracy of the estimated value and at least one of an upper limit of a confidence interval and a lower limit of the confidence interval, wherein the displayed confidence interval limit is calculated based at least in part upon a predetermined confidence level or the information received from the sensor.

2. The method of claim 1 further comprising:
    receiving a user selection, via a user interface of the patient monitor, selecting the predetermined confidence level.

3. The method of claim 1, wherein displaying the at least one statistical parameter comprises:
    displaying the upper limit of the confidence interval, the lower limit of the confidence interval, and the accuracy of the estimated value on the display.

4. The method of claim 1, wherein displaying the at least one statistical parameter comprises:
    displaying the predetermined confidence level on the display.

5. The method of claim 3 further comprising:
    displaying a representation of a dial having a circumference with an associated scale on the display;
    displaying an arrow pointing to a first position on the circumference corresponding to the estimated value of the oxygen saturation of the patient's blood on the display;
    displaying a first mark on the circumference at a second position corresponding to the upper limit of the confidence interval on the display;
    displaying a second mark on the circumference at a third position corresponding to the lower limit of the confidence interval on the display; and
    adjusting a displayed feature of the arrow based on the accuracy.

6. The method of claim 3 further comprising:
    displaying a bar with an associated scale on the display;
    displaying a first mark at a first position on the bar corresponding to the estimated value of the oxygen saturation of the patient's blood on the display;
    displaying a second mark at a second position on the bar corresponding to the upper limit of the confidence interval on the display;
    displaying a third mark at a third position on the bar corresponding to the lower limit of the confidence interval on the display; and
    displaying the first mark with a size corresponding to the accuracy of the estimated value of the oxygen saturation of the patient's blood on the display.

7. A method for display of a physiological parameter comprising, using a processor configured to determine the physiological parameter, wherein the processor is associated with a patient monitor, and wherein determining the physiological parameter comprises:
    calculating, using the processor, an estimated value of the physiological parameter based at least in part upon physiological data received from a sensor;
    displaying a graphical representation comprising a numerical scale on a display of the patient monitor;
    displaying a first indicator on the graphical representation at a first position relative to the numerical scale corresponding to the estimated value of the physiological parameter; and
    displaying a second indicator on the display describing a probability distribution of the estimated value of the physiological parameter, wherein displaying the second indicator comprises displaying the second indicator on the graphical representation at a second position relative to the numerical scale corresponding to an upper limit of a confidence interval or a lower limit of the confidence interval associated with the estimated value of the physiological parameter.

8. The method of claim 7, wherein displaying the second indicator further comprises:
    identifying a predetermined confidence level, wherein the upper limit or lower limit is calculated based at least in part upon the predetermined confidence level and the physiological data received from the sensor.

9. The method of claim 7, comprising displaying a third indicator on the graphical representation, wherein the second position of the second indicator corresponds to the upper limit of the confidence interval, and wherein displaying the third indicator comprises displaying the third indicator at a third position relative to the numerical scale corresponding to the lower limit of the confidence interval.

10. The method of claim 7 further comprising:
displaying a third indicator describing an accuracy of the estimated value on the display.

11. The method of claim 10, wherein displaying the third indicator further comprises:
calculating, using the processor, a standard deviation of the physiological data received from the sensor; and
generating, using the processor, the third indicator based on the standard deviation.

12. The method of claim 7 further comprising:
displaying the probability distribution of the estimated value of the physiological parameter.

13. The method of claim 7, wherein the graphical representation comprises a bar adjacent to and parallel with the numerical scale.

14. The method of claim 7, wherein the graphical representation comprises a graphical representation of a dial, and wherein the numerical scale is disposed about a circumference of the graphical representation of the dial.

15. The method of claim 14 further comprising:
displaying the first indicator as an arrow within the graphical representation of the dial pointing to the estimated value of the physiological parameter; and
displaying the second indicator as a bar on the circumference of the graphical representation of the dial.

16. The method of claim 7 comprising:
audibly communicating the estimated value of the physiological parameter.

17. The method of claim 7 comprising:
calculating, using the processor, an accuracy of the estimated value of the physiological parameter.

18. The method of claim 17 further comprising:
generating one or more audible tones having at least one of a pitch, an amplitude, a duration, and a separation period selected based on the accuracy of the physiological parameter.

19. A monitor, comprising:
a processor configured to:
calculate an estimated value of oxygen saturation of a patient based at least in part upon information received from a sensor;
calculate an accuracy of the estimated value based at least in part upon one or more data characteristics of the information received from the sensor, wherein the one or more data characteristics comprise a pulse amplitude, a pulse shape, or a correlation of infrared and red components; and
calculate at least one of an upper limit of a confidence interval or a lower limit of the confidence interval, wherein the upper limit or the lower limit of the confidence interval is calculated based at least in part upon a predetermined confidence level or information received from the sensor; and
a display configured to display the estimated value, the accuracy, and the upper limit or the lower limit of the confidence interval.

20. The method of claim 12, wherein the probability distribution comprises a first curve describing a first probability that an actual value of the physiological parameter is less than the estimated value of the physiological parameter, and wherein the probability distribution comprises a second curve-describing a second probability that the actual value of the physiological parameter is greater than the estimated value of the physiological parameter.

* * * * *